(12) United States Patent
Mather

(10) Patent No.: US 9,453,501 B2
(45) Date of Patent: Sep. 27, 2016

(54) REVERSIBLE SHAPE MEMORY POLYMERS EXHIBITING AMBIENT ACTUATION TRIGGERING

(71) Applicant: Patrick T. Mather, Oxford, PA (US)

(72) Inventor: Patrick T. Mather, Oxford, PA (US)

( * ) Notice: Subject to any disclaimer, the term of this patent is extended or adjusted under 35 U.S.C. 154(b) by 0 days.

(21) Appl. No.: 14/771,928

(22) PCT Filed: Mar. 4, 2014

(86) PCT No.: PCT/US2014/020277
§ 371 (c)(1),
(2) Date: Sep. 1, 2015

(87) PCT Pub. No.: WO2014/138049
PCT Pub. Date: Sep. 12, 2014

(65) Prior Publication Data
US 2016/0017870 A1    Jan. 21, 2016

Related U.S. Application Data

(60) Provisional application No. 61/771,970, filed on Mar. 4, 2013.

(51) Int. Cl.
*F03G 7/06* (2006.01)
*B29C 51/10* (2006.01)
(Continued)

(52) U.S. Cl.
CPC ............. *F03G 7/065* (2013.01); *B29C 51/002* (2013.01); *B29C 51/10* (2013.01); *C08J 5/00* (2013.01); *A61L 2400/16* (2013.01); *B29K 2021/006* (2013.01); *C08J 2300/12* (2013.01); *C08J 2300/26* (2013.01)

(58) Field of Classification Search
CPC ..... F03G 7/065; B29C 51/10; B29C 51/002; C08J 5/00; C08J 2300/12; C08J 2300/26; B29K 2021/006; A61L 2400/16

USPC .............. 60/527–529; 310/306–307; 29/428, 29/592.1
See application file for complete search history.

(56) References Cited

U.S. PATENT DOCUMENTS 5,964,744 A  * 10/1999 Balbierz ................. A61L 27/34
                                                              604/530
6,720,402 B2    4/2004 Langer et al.
(Continued)

FOREIGN PATENT DOCUMENTS

JP            01204719        8/1989

OTHER PUBLICATIONS

International Preliminary Report on Patentability Form PCT/IB/220, International Application No. PCT/US2014/020277, pp. 1-6, Dated Dec. 12, 2014.

*Primary Examiner* — Hoang Nguyen

(57) ABSTRACT

Shape memory polymers featuring reversible actuation capability under ambient stimulus for integration with apparel. One approach is to use a multiblock polymer consisting of two (or potentially more) blocks in which the one block is the crystalline switching block with relatively low melting transitions, the other block has a higher thermal transition, and the two blocks are linked together by a linker molecule. Another approach is to use a graft copolymer having high and low melting transitions where the graft copolymer has a first polymer serving as the backbone and a second polymer being grafted to or from the backbone at certain graft locations. A further approach is to use latent crosslinking of a semicrystalline polymer with reactive groups placed on the backbone. Finally, these polymers may be formed as actuators that undergo curling, twisting and even volumetric expansion.

20 Claims, 25 Drawing Sheets

(51) Int. Cl.
  *C08J 5/00* (2006.01)
  *B29C 51/00* (2006.01)
  *B29K 21/00* (2006.01)

(56) References Cited

U.S. PATENT DOCUMENTS

| | | | | |
|---|---|---|---|---|
| 8,198,369 B2 * | 6/2012 | Xie | ............ | C08J 7/04 521/178 |
| 8,237,324 B2 * | 8/2012 | Pei | ............ | H01L 41/094 310/306 |
| 8,394,393 B2 * | 3/2013 | Mather | ............ | A61K 47/48976 264/465 |
| 8,881,521 B2 * | 11/2014 | Browne | ............ | D07B 1/0673 57/237 |
| 2009/0280330 A1 | 11/2009 | Xie et al. | | |
| 2010/0181698 A1 | 7/2010 | Berger et al. | | |
| 2010/0240841 A1 | 9/2010 | Shimura et al. | | |

* cited by examiner

REVERSIBLE SHAPE MEMORY POLYMERS EXHIBITING AMBIENT ACTUATION TRIGGERING

CROSS-REFERENCE TO RELATED APPLICATIONS

This application claims priority to U.S. Provisional Application No. 61/771,970, filed on Mar. 4, 2013.

BACKGROUND OF THE INVENTION

1. Field of the Invention

The present invention relates to shape memory polymers and, more particularly, to shape memory polymers featuring reversible actuation capability under ambient stimulus for integration with apparel.

2. Description of the Related Art

Shape memory materials are those materials that have the ability to "memorize" a macroscopic (permanent) shape, be manipulated and "fixed" to a temporary and dormant shape under specific conditions of temperature and stress, and then later relax to the original, stress-free, condition under thermal, electrical, or environmental command. This relaxation is associated with elastic deformation stored during prior manipulation. Shape memory materials have aroused great attention by scientists and engineers due to their capacity to remember two shapes at different conditions.

The most prominent and widely used shape memory materials currently are shape memory alloys (SMAs). Their shape memory effect comes from the existence of two stable crystal structures: the high temperature-favored austenitic phase and low temperature-favored (and "yield-able") martensitic phase. Downsides that limit their application include limited recoverable strains less than 8%, inherently high stiffness, high cost, comparatively inflexible transition temperature, and demanding processing and training conditions. Such limitations have provided motivation for the development of alternative materials, especially polymeric shape memory materials. Polymeric materials are intrinsically capable of a shape memory effect, although the mechanisms responsible differ dramatically from those of metal alloys. In SMAs, pseudoplastic fixing is possible through the martensitic de-twinning mechanism, while recovery is triggered by the martensite-austenite phase transition. In contrast, shape memory polymers achieve temporary strain fixing and recovery through a variety of physical means, while the underlying extensibility is derived from the intrinsic elasticity of polymeric networks.

The shape memory effect in polymers can take two quite distinct forms: one-way or two-way shape memory. In the one-way shape memory case, the cycle is started at low stress and high temperature, at which point the stress ramped to deform the sample, and following which steps of cooling under load and then unloading at low temperature reveal the quality of shape "fixing". Finally, reheating the sample to the original temperature leads to strain recovery. In contrast, two-way shape memory features reversible actuation at a single applied stress, as shown in FIG. 1b. The two-way shape memory case is the one most easily exploited for actuation purposes of interest for the present invention, while one-way shape memory is required for controlled, one-time deployment events, such as expansion of slender medical device or unfolding of a complex structure. In the present application, one-way and two-way shape memory are referred to as 1 W-SM and 2 W-SM, respectively. However, no 2 W-SM polymer has been reported to date that would allow ambient (or environmental) stimulus at temperatures in the 20-40° C. range and with amenability for integration with fabric.

BRIEF SUMMARY OF THE INVENTION

In accordance with the foregoing objects and advantages, the present invention provides a polymer having several critical "ingredients" to achieve reversible actuation, namely, crystallizable network chains, crosslinking (physical or covalent), and stress bias. In addition, the present invention involves polymers that can crystallize at a temperature near ambient temperatures and with minimal undercooling (hysteresis). Further, the present invention involves multiple ways to crosslink the constituent polymer chains, recognizing that physical crosslinks offer processing flexibility combined with imperfect memory (reversibility), while covalent crosslinks feature near-perfect memory but with processing demands that may or may not be amenable to apparel manufacturing. Three groups of polymers that may be used for the present invention have been conceived and, within those groups, the primary compositional variables have been identified. Some polymers may feature the best combination of synthesis "robustness," processability, and reversible shape memory, the latter including actuation force, actuation strain, cycle fatigue, among others.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
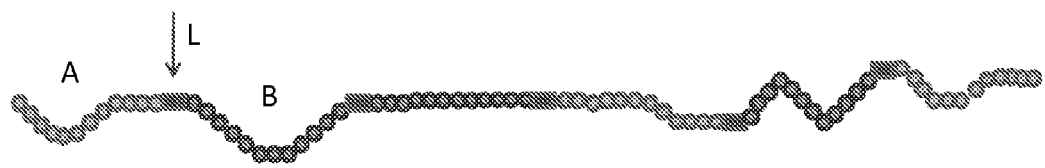
FIG. 1 is a schematic of a multiblock polymer according to the present invention.

Referring now to the drawings, wherein like reference numerals refer to like parts throughout, there is seen in FIG. 1 a schematic a multiblock approach to synthesizing a shape memory polymer according to the present invention. The multiblock polymer of FIG. 1 consists of two (or potentially more) blocks in which the "A" block is the crystalline switching block with relatively low melting transitions, the "B" block with a higher thermal transition (Tg or Tm), and the two are linked together by a linker molecule, "L". This multiblock polymer can be prepared by known polymer chemistry and using commercially available or easily synthesized "A" and "B" blocks. For example, the primary synthetic variables include: the composition and molecular weight of each block, the weight percentage of block "B", $w_B$ (noting $w_A + w_B = 100\%$), and the total molecular weight of the multiblock polymer. It is recognized that the composition and molecular weight of each block will impact their melting points. This is particularly important for the "A" block since that will regulate the actuation and recovery temperatures, which need to be near ambient temperature. Consequently, both the composition and molecular weight of the "A" block can be varied. Initially, the present invention envisions holding fixed the value of $w_B$ at 30% and the composition of the B block such that the Tm value for that block are satisfied. A $3^{rd}$ block or modification to the linker molecule, L, can be introduced to enable the polymers to be dispersed in a waterborne suspension (or ink) if that process is deemed useful for particular applications.

This multiblock polymer embodiment will yield a shape memory thermoplastic that can be processed by heating to a molten or tacky state and then flowing or bonding the polymers by conventional means. Flow by extrusion, molding, or fiber spinning will be possible only above the second (higher) melting temperature of the multiblock material. The viscosity in that state will be strongly dependent on total polymer molecular weight, as $\eta \sim M^{3.5}$. Tackiness related to a heat transfer process will be highest at a temperature above both thermal transitions of the constituent blocks. Addition of "A" homopolymer to the multiblock polymer in the form of a blend may offer advantages to the heat transfer bonding process. Finally, electrospinning or blown fiber processing is possible with this polymer with little development work required.

This multiblock polymer embodiment will feature two thermal transitions associated stepwise decrease in elastic modulus upon heating. More importantly, reversible actuation should be witnessed when films or fibers of the material are heating (contracting) and cooled (elongating) to melt and recrystallize the "A" block, respectively. Because the "B" block functions as the phase (30% in this design) that physically crosslinks the material, its rigidity relative to the rubbery "A" phase at temperature between the two thermal transitions is of paramount importance. Compared to covalently crosslinked materials, this approach is intrinsically subject to creep (continuous deformation under load) that may slightly compromise the return actuation (return to home position) with each additional cycle. Testing should reveal how much cycle-to-cycle creep actual occurs for different compositions.

The "A" block needs to have a melting transition that is above room temperature and below approximately 50° C. The molecular weight should be in the range from 2000 g/mol and 100,000 g/mol, preferably between 3500 g/mol and 30,000 g/mol. Compositions for this block can include the following, noting that the molecular weight of each will significantly alter the melting point: poly($\epsilon$-caprolactone), poly(ethylene oxide), poly(cyclooctene), poly(1,5-cyclooctadiene), poly(cyclooctene-co-cycloctadiene) (random copolymer), poly(trans-butadiene), poly(glycolide), poly(dioxanone), poly(hydroxy butyrate), nylon-6, nylon-4,6, nylon-6,6, nylone-6,10, nylon-11, nylon-12, poly(butene-1), poly(stearyl acrylate), poly(diethyl siloxane), poly(1,3-dioxolane), poly(ethylene imine), poly(hexene-1), poly(trans-1,4-isoprene), poly(4-methyl pentene-1), stereoblock poly (propylene), poly(tetrahydrofuran), poly(trimethylene oxide), and poly(vinyl methyl ether).

The "B" block should be semicrystalline and of similar molecular weight ranges as listed for polymer "A". Thus, it can be selected from the entire list above for block "B", but with the requirement that pair of "A" and "B" feature a higher melting point for "B". The melting point should be higher by at least 10° C., preferably 50° C. higher. The "B" block can also be an amorphous polymer with molecular weight in the range from 2000 g/mol and 100,000 g/mol, preferably between 3500 g/mol and 30,000 g/mol. The glass transition temperature, Tg, should be higher than the Tm of block "A" by at least 10° C., pre preferrably 50° C. higher. The amorphous block "B" can be selected from this list: poly(styrene), poly(methyl methacrylate), poly(phenylene oxide), poly(carbonate), poly(alkyl methacrylate), poly (alkyl acrylate), polysulfone, poly(acrylonitrile), poly(ether sulfone), polyhedral oligosilsequioxane (POSS) polymers, poly(vinyl acetate), poly(vinyl alcohol), poly(vinyl butyral), poly(vinyl chloride), and poly(N-vinyl carbazole).

The linker "L" can be a direct bond between blocks "A" and "B" in the form of carbon-carbon single, double, and triple blonds, or multi-atom linkages including but not limited to: ether, ester, sulfide, carbonate, urethane, urea, and amide. Molecular linkers may be used as an alternative to direct block-block linkage to link blocks "A" and "B" together and include, diisocyanates, diols, dicarboxylic acids, and dienes. Linker "L" may also comprise a polyether block amide (PEBAX® available from Arkema of King of Prussia, Pa.).

Figure 2:
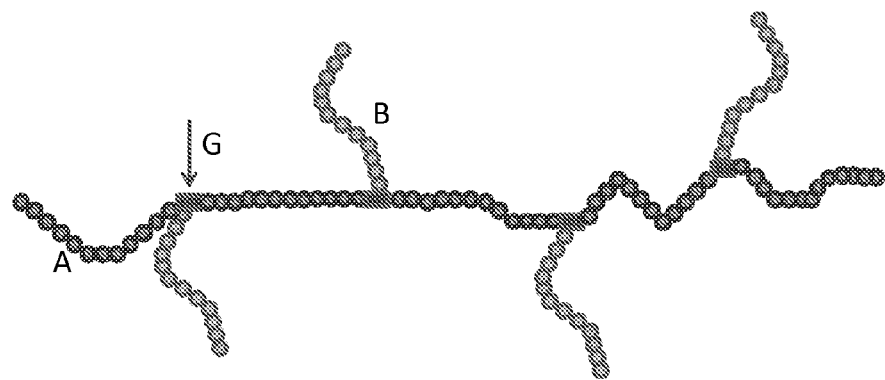
FIG. 2 is a schematic of a graft copolymer according to the present invention.

Referring to FIG. 2, the present invention also encompasses a graft copolymer having high and low melting transitions. In this embodiment of the present invention, the graft copolymer has polymer "A" serving as the backbone and polymer "B" being grafted to or from the backbone at the graft locations, "G". As in the first embodiment, the "A" segment is the switching segment, while "B" forms a distinct hard phase that physically crosslinks the material. The graft copolymer approach of the present invention uses a distinct architecture that places the higher thermal transition macromer groups on the backbone of the crystallizable polymer in the form of a graft (or "comb") copolymer. Such polymers can be made using three approaches: (i) a grafting from, (ii) grafting to, or (iii) a macromer approach. One of these approaches may be selected after careful consideration of the relative merits of each approach, such as through the use of graft copolymer literature outside of the SMP field. For example, one implementation of this approach is a simple B-A-B triblock copolymer.

In this embodiment, the primary synthetic variables include: the composition of blocks A and B, the backbone molecular weight, the graft molecular weight, and the grafting density. Here, the grafting density is inversely proportional to the molecular weight between grafting sites, which is our directly controllable variable. Further, the combination of grafting density and graft (B) molecular weight will give $w_B$, which will be targeted at 30%, as in the first approach. This approach will yield a shape memory thermoplastic that is amenable to molding, extrusion, and fiber processing. Heat transfer bonding is expected to be good, but possible only by heating above both thermal transitions. The viscosity should be somewhat lower for this polymer compared to the multiblock approach, owing to the architecture that somewhat disfavors entanglements.

This embodiment should feature two thermal transitions and a profound decrease in elastic modulus as the melting transition of the backbone, "A", is exceeded. Above Tm or Tg of the grafted polymer, we anticipate that the materials will transform to a viscoelastic liquid for processing. Thermal cycling about the backbone melting temperature and with applied tensile load will lead to actuation strain that depends on both the load and the grafting density. It is quite unclear which architecture among the first two approaches will feature larger strain and which one will feature larger actuation force; thus, experimental comparison is required.

In this embodiment, block "A" needs to have a melting transition that is above room temperature and below approximately 50° C. The molecular weight should be in the range from 2000 g/mol and 100,000 g/mol, preferrably between 3500 g/mol and 30,000 g/mol. Compositions for this block can include the following, noting that the molecular weight of each will significantly alter the melting point: poly(ε-caprolactone), poly(ethylene oxide), poly(cyclooctene), poly(1,5-cyclooctadiene), poly(cyclooctene-co-cycloctadiene) (random copolymer), poly(trans-butadiene), poly(glycolide), poly(dioxanone), poly(hydroxy butyrate), nylon-6, nylon-4,6, nylon-6,6, nylone-6,10, nylon-11, nylon-12, poly(butene-1), poly(stearyl acrylate), poly(diethyl siloxane), poly(1,3-dioxolane), poly(ethylene imine), poly(hexene-1), poly(trans-1,4-isoprene), poly(4-methyl pentene-1), stereoblock poly(propylene), poly(tetrahydrofuran), poly(trimethylene oxide), and poly(vinyl methyl ether).

The grafted block "B" should be semicrystalline and of similar molecular weight ranges as listed for polymer "A". Thus, it should be selected from the entire list above for block "B", but with the requirement that pair of "A" and "B" feature a higher melting point for "B". The melting point should be higher by at least 10° C., preferably 50° C. higher. The "B" block can also be an amorphous polymer with molecular weight in the range from 2000 g/mol and 100,000 g/mol, preferably between 3500 g/mol and 30,000 g/mol. The glass transition temperature, Tg, should be higher than the Tm of block "A" by at least 10° C., preferably 50° C. higher. The amorphous block "B" can be selected from this list: poly(styrene), poly(methyl methacrylate), poly(phenylene oxide), poly(carbonate), poly(alkyl methacrylate), poly(alkyl acrylate), polysulfone, poly(acrylonitrile), poly(ether sulfone), polyhedral oligosilsequioxane (POSS) polymers, poly(vinyl acetate), poly(vinyl alcohol), poly(vinyl butyral), poly(vinyl chloride), and poly(N-vinyl carbazole).

The grafting point "G" can be a direct bond between backbone block "A" and grafting block "B" in the form of carbon-carbon single, double, and triple blonds, or multi-atom linkages including but not limited to: ether, ester, sulfide, carbonate, urethane, urea, and amide. Molecular linkers may be used as an alternative to direct block-block linkage to graft block "B" to block "A" and include triisocyanates, triols, tricarboxylic acids, and trienes.

Figure 3:
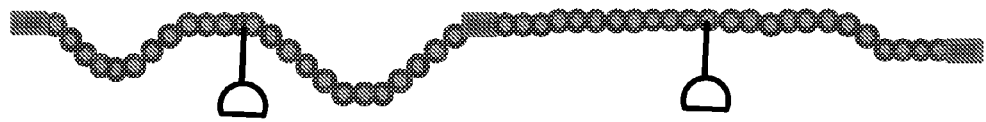
FIG. 3 is a schematic of a semicrystalline polymer with latent crosslinking of reactive groups according to the present invention.

Referring to FIG. 3, the present invention also encompasses latent crosslinking of a semicrystalline polymer with reactive groups (black crosses) placed on the backbone. This crosslinkable group can be chosen from among a variety of crosslinking strategies documented in the literature. In this embodiment, the primary synthetic variables include: the composition of blocks A, the backbone molecular weight, and concentration of crosslinkable groups. Further, the composition of the crosslinker itself is a variable. There are several semicrystalline polymers that are intrinsically crosslinkable and they will be considered carefully as candidates, given the associated synthetic simplicity. Additives (such as peroxides or other) may be required for crosslinking.

In this embodiment, the "backbone" block needs to have a melting transition that is above room temperature and below approximately 50° C. The molecular weight should be in the range from 2000 g/mol and 100,000 g/mol, preferrably between 3500 g/mol and 30,000 g/mol. Compositions for this block can include the following, noting that the molecular weight of each will significantly alter the melting point: poly(ε-caprolactone), poly(ethylene oxide), poly(cyclooctene), poly(1,5-cyclooctadiene), poly(cyclooctene-co-cycloctadiene) (random copolymer), poly(trans-butadiene), poly(glycolide), poly(dioxanone), poly(hydroxy butyrate), nylon-6, nylon-4,6, nylon-6,6, nylone-6,10, nylon-11, nylon-12, poly(butene-1), poly(stearyl acrylate), poly(diethyl siloxane), poly(1,3-dioxolane), poly(ethylene imine), poly(hexene-1), poly(trans-1,4-isoprene), poly(4-methyl pentene-1), stereoblock poly(propylene), poly(tetrahydrofuran), poly(trimethylene oxide), and poly(vinyl methyl ether).

The backbone of this approach can be crosslinked to adjacent polymeric backbone through carbon-carbon single, double, and triple blonds, or multi-atom linkages including but not limited to: ether, ester, sulfide, carbonate, urethane, urea, and amide. Molecular linkers may be used as an alternative to direct backbone-backbone linkage include diisocyanates, diols, dicarboxylic acids, and dienes.

Polymers in this embodiment will require a two-step process: first forming the primary shape by a thermal process and then a second step for setting the permanent shape. This second step will either be a thermal annealing or irradiation from UV light, electron beam, or gamma radiation. It is during this crosslinking that covalent bonds between chains are established, imparting upon the polymer excellent shape memory.

This polymer is expected to feature the best shape memory and actuation characteristics at the expense of a more complicated process, namely the two-step mold, then crosslink processing. The resulting materials are expected to feature reversible melting/crystallization phase behavior with a melting transition that is manipulated by both the polymer backbone composition and the crosslink density.

Shape memory polymers according to the present invention may have their molecular and basic physical properties characterized and evaluated using the following tests to determine whether and how they can form actuators according to the present invention. First, GPC will be used to measure the molecular weights (Mn and Mw) of the polymers synthesized. As Mw is strongly correlated with strength and durability of a polymer, while also increasing viscosity, we will seek to optimize the molecular weight of polymers synthesized in an iterative manner involving the sequence: synthesis, GPC characterization, synthesis repetition, etc. Second, Fourier-Transform Infrared Characterization (FT-IR) and $^1$H NMR may be used to measure the relative incorporation levels of different molecular and macromolecular component into the polymers. Because reactivities are not all the same among regents utilized, it is likely that the incorporation levels will be different than those targeted and thus utilized in the polymerization reactions. Third, differential scanning calorimetry (DSC) may be used to measure the melting transitions and glass transitions of the synthesized polymers, adjusting composition as needed to fine tune the melting and crystallization temperatures of the switching phase. Crystallization kinetics will be estimated from the hysteresis in Tc vs. Tm (lower hysteresis indicating faster crystallization). Fourth, x-ray diffraction analysis may be used to measure the degree of crystallinity for crystalline phases within each material using wide-angle x-ray diffraction and associated standard methods. X-ray diffraction will be helpful in comparing degrees of crystallinity, degrees of orientation, and crystallization kinetics (complementing DSC) for those samples that are strong candidates for selection for advanced studies but for which there exists a need to fine-tune crystallization behavior. Fifth, dynamic mechanical analysis (DMA) may be used to gather tensile storage modulus and loss tangent data that will reveal the sharpness of the switching segment's thermal transition, along with the flatness and magnitude of the elastic rubbery plateau between the two thermal transitions. Tensile creep may also be measured in this temperature window. All such DMA data will be highly pertinent to the shape memory cycle testing and compositions should only advance to such testing if DMA results look favorable (especially transition sharpness and rubber plateau flatness). Finally, tensile testing may be performed as durability of the polymers is a must and this will be assessed using ultimate tensile testing with the Linkam TST-350 apparatus. Thus, for each composition, it is possible to measure the Young's modulus, yield stress, elongation at break, and engineering toughness. Those materials that combine good reversible actuation with high toughness will be highly ranked from among the candidates for transition to next levels of investigation.

The reversible shape memory characteristics may be characterized using published techniques, see *Macromolecules* 41, pp. 184-192 (2008), hereby incorporated by reference, using a TA Instruments Q800 apparatus to thermally cycle the SMPs of the present invention and measure the resulting actuation strains. Thus, strain versus temperature loops will be produced for a range of compositions selected from prerequisite thermal and DMA testing and with variation in heating and cooling rate (0.5, 1, 2, and 5° C./min) as well as variation in the applied tensile load. Figures-of-merit may be established for such testing and the materials synthesized ranked for their merit. Initial figures-of-merit included actuation strain at a set stress (1 MPa, for example), thermal hysteresis ($\Delta T = T_{contract} - T_{elongate}$), and actuation stress. The latter will be ascertained by the x-axis intercept of actuation strain versus applies stress, revealing the "upper bound" stress where no actuation occurs at all due to the limited capacity of the elastic rubber phase to contract upon heating.

Free standing actuation has been demonstrated in the form of a bimorph combining crosslinked poly(cyclooctene) and an elastomer. Reversible, with significant (visually detectable) and repeatable bending, actuation was possible with this simple approach. In the course of that research, it was learned through both experimentation and numerical modeling that: (i) significant hysteresis exists in the actuation, (ii) the moduli, stored SMP strain (prior to bonding), and thicknesses of the two layers are critically important parameters determining the actuation amplitude, there quantified via the sample tip deflection. For polymeric, reversible actuators, the present invention extends this work to design material combinations that bend/curl, twist, and expand reversibly. For example, crosslinked PCO as the 2 W-SMP may be used due to its immediate availability. As available from the above polymer development, crosslinked PCO may be incorporated as actuators according to the present invention.

The components discussed above may be formed into reversible shape memory polymer actuators according to the present invention. Ideally, the components are selected so that the actuator transition occurs between −10 degrees Celsius and 50 degrees Celsius. It is preferred that the actuator transition occur between 10 degrees Celsius and 30 degrees Celsius.

Figure 4A:
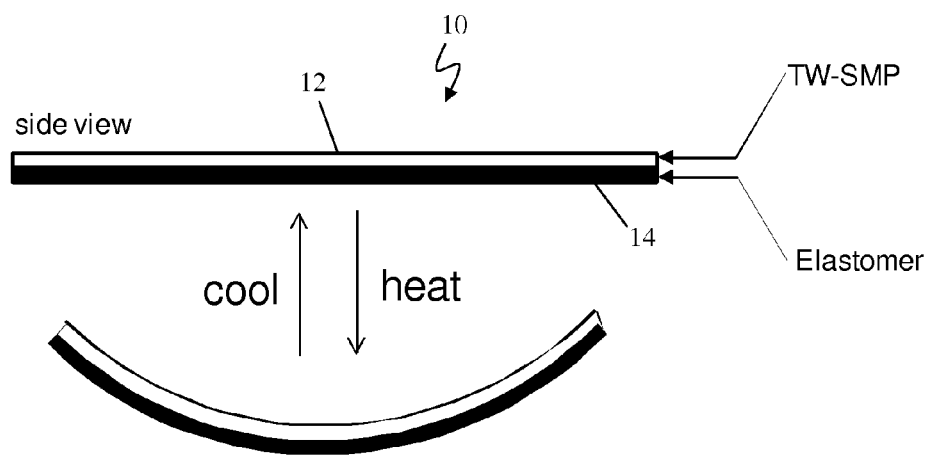
FIG. 4A is a schematic of a bimorph curling actuator comprising strained 2 W-SMP and stress-free elastomer are bonded together.
Figure 4B:
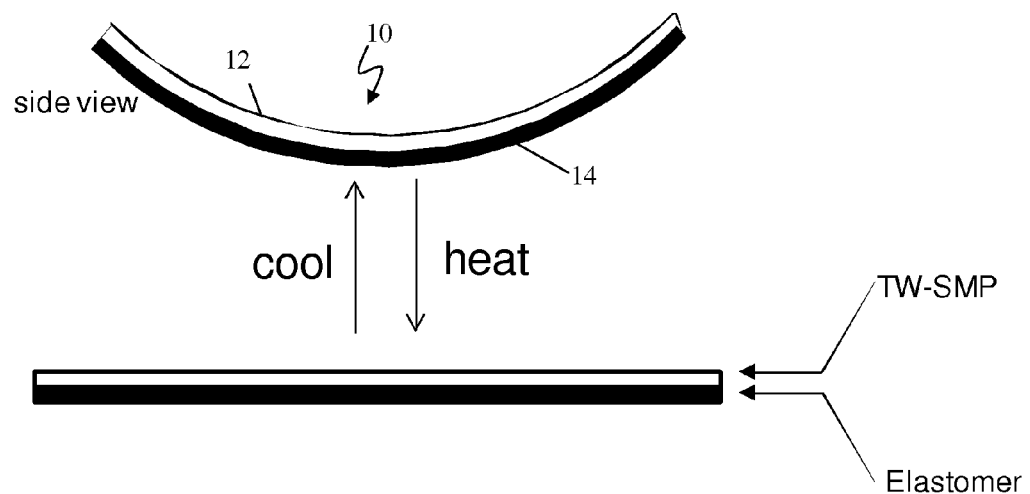
FIG. 4B is another embodiment of a bimorph curling actuator comprising strained 2 W-SMP and stress-free elastomer are bonded together.

As seen in FIGS. 4A and 4B, an actuator 10 may comprise a first layer 12 comprised of a shape memory polymer and a second layer 14 comprised of a resilient elastomer 14 bound to first layer 12. In FIG. 4A, actuator 10 is configured to be in a linear (flat) state at a first, cooler temperature and in a curved state in a second, warmer temperature. This actuation is accomplished by training the first layer 12 to have a curved configuration above the shape memory transition temperature of the shape memory polymer, which may be the glass transition temperature or the melting temperature depending on whether the shape memory polymer is crystalline or amorphous. The fixing of a permanent shape above the transition temperature is referred to as the fixed shape or configuration. The actuation is then completed by using second layer 14 that is configured to be in a linear shape below the shape memory transition temperature and thus applies a biasing force to first layer 12 when actuator 10 is cooled below the transition temperature. When actuator 10 is heated to be at or above the shape memory transition temperature, first layer 12 will undergo the shape memory change into the curved state and overcome the biasing force of second layer 14 to move into a curved configuration. When actuator 10 is cooled, the biasing force of second layer 14 will return actuator 10 to the linear configuration. In FIG. 4B, the actuation is reversed so that first layer 12 is trained to have linear configuration at the transition temperature and second layer 14 biases first layer 12 into a curved configuration below the transition temperature. Thus, actuator 10 will flatten in response to heating above the transition temperature and return to the curved configuration when cooled below that temperature.

In selecting the biasing layer composition and designing the two-layer actuator, it is important that each layer's stiffness be approximately the same. Here, the bending stiffness is calculated for beam-shaped films with a rectangular cross-section as the product of Young's modulus, E, and geometric moment of inertia, I. Specifically, E*I=E*(b*h$^3$)/12, where b is the beam (or film) width and h is the beam (or film) thickness.

Acceptable elastomers for actuators according the present invention include acrylates, such as tBA-PEGDMA to have a Young's modulus of about 13.9 MPa and a glass transition temperature of −10 degrees Celsius. The elastomer can also comprise various other acrylates, laminated matrix materials (PEBAX), neopentyl glycol propoxylate diacrylate (NGPDA), and trimethylolpropane ethoxylate triacrylate. Other elastomers anticipated to function well as the biasing layer are those with elastic modulus in the range of 1-20 MPa and a glass transition temperature lower than −10 degrees Celsius, including silicone rubber (crosslinked poly(dimethyl siloxane)), styrene-butadiene rubber, acrylic elastomers, epoxy elastomers, hydrogels (water-swollen polymer networks), crosslinked polybutadiene, crosslinked polyisoprene, crosslinked natural rubber, and crosslinked polyisobutylene.

Bonding of the elastomeric selected biasing layer with the shape memory polymer is conducted by first fixing the shape memory polymer to a desired uniaxial or biaxial tensile strain, then curing the elastomeric layer from an initially liquid (uncured) state upon the strain-fixed shape memory polymer in a mold. Alternatively, solid elastomeric layers are bonded to the strain-fixed shape memory polymer using an adhesive. For curling actuators (those that curl upon heating), the SMP is bonded to a flat biasing layer. For flattening actuators, (those that flatten upon heating), the SMP is bonded to the outer surface of an initially curled elastomer. The value of uniaxial or biaxial strain fixed in the shape memory polymer prior to bonding is selected to yield the desired curling or flattening behavior during heating and cooling. This strain will vary between 1% and 100%, preferably between 10% and 30%. The optimal value will depend on the bending stiffness of the SMP and biasing layer, increasing as the latter increases to yield useful reversible shape changes.

Figure 5:
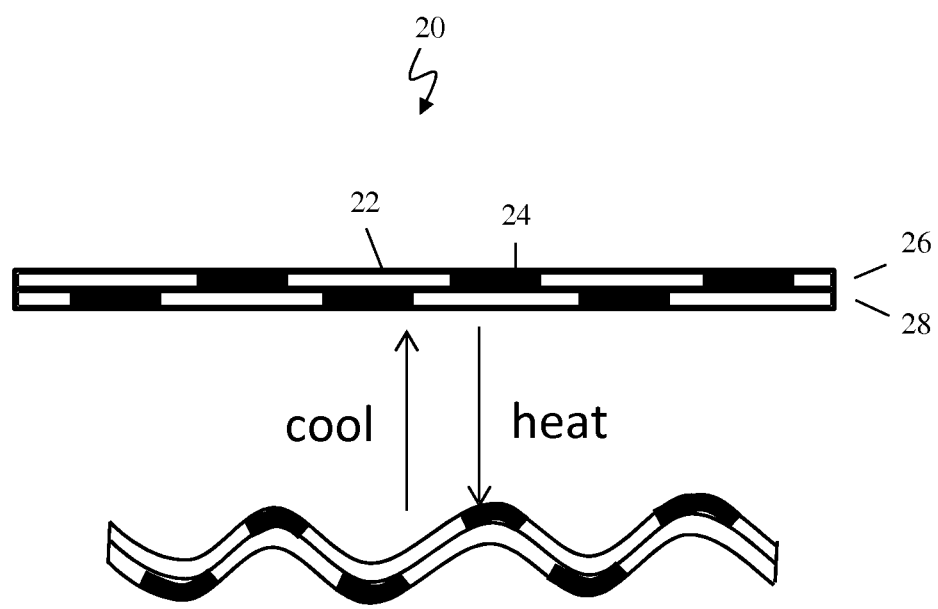
FIG. 5 is a schematic of a linear actuator design using curvature actuation alternation along the specimen length.

Referring to FIG. 5, the present invention also includes a linear wrinkling actuator 20 composed of a series of alternating shape memory segments 22 and elastomer segments 24 that form both a first layer 26 and second layer 28 so shape memory segments 22 and elastomer segments 24 of first layer 26 are staggered with respect to shape memory segments 22 and elastomer segments 24 of second layer 28.

Figure 6:
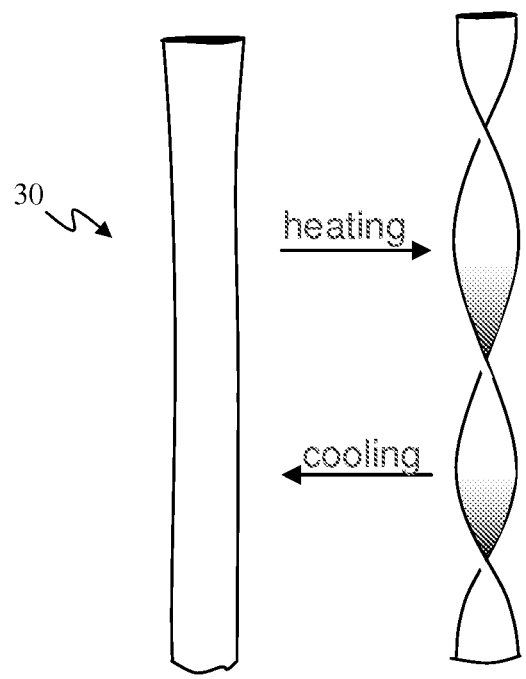
FIG. 6 is a schematic of a twisting actuator based on asymmetric stacking of SMP and elastomer elements (details not shown)

Referring to FIG. 6, twisting actuators 30 may formed by lamination of SMP and elastomer with non-symmetric stacking so that as the shape memory polymer element contracts, the laminated structure will twist 6. A large collection of actuators 30 may collectively expand in volume reversibly and be useful for integration into product concepts where volumetric expansion and contraction is desired. Variables that may be implemented include the pitch of the shape memory polymer, thickness ratio of shape memory polymer and elastomer, and width of the shape memory polymer.

Figure 7:
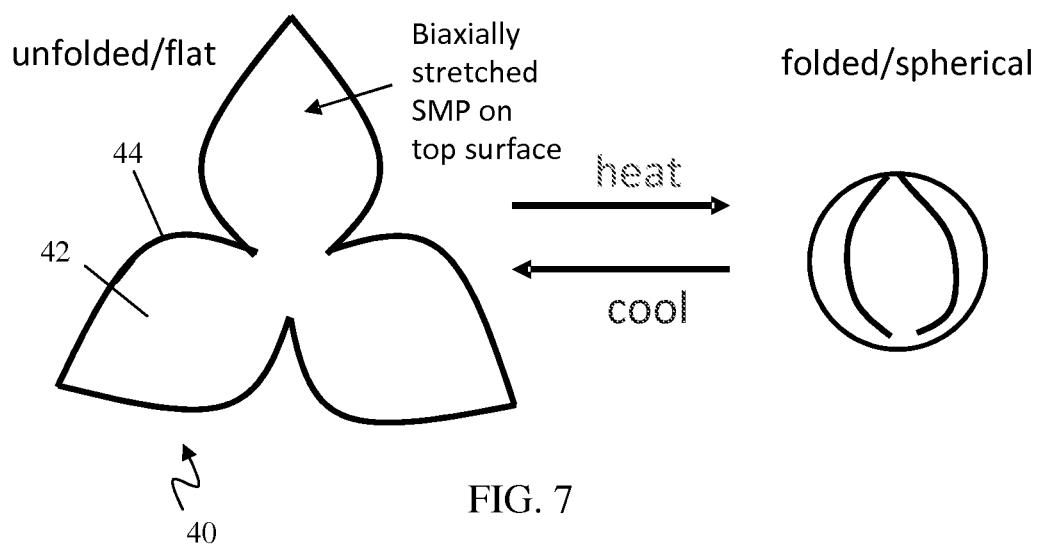
FIG. 7 is a schematic of a volumetric actuator based on stack-and-cut bimorphs where the SMP layer is biaxially oriented before bonding.

Three-dimensional, volumetric actuators 40 inspired by origami principles are also encompassed by the present invention. Referring to FIG. 7, three-dimensional actuators 40 apply the biomorph approach of FIGS. 4A and 4B to sheets that are cut, manually or by a laser, to fold into advantageous shapes when heated. In one design, for example, a sheet 42 of the layered shape memory polymer and elastomer of FIG. 4A may include cuts 4 that match the curvature radius of a folded sphere. Importantly, the cold configuration is flat, while the hot configuration is round and thus takes up more volume. Intermediate shapes between the two extremes may be useful for consideration. In the course of designing volumetric actuators, known origami literature may be used to identify cutting patterns associated with particular folded shapes, including boxes, tetrahedral, spheroids, among others.

Figure 8:
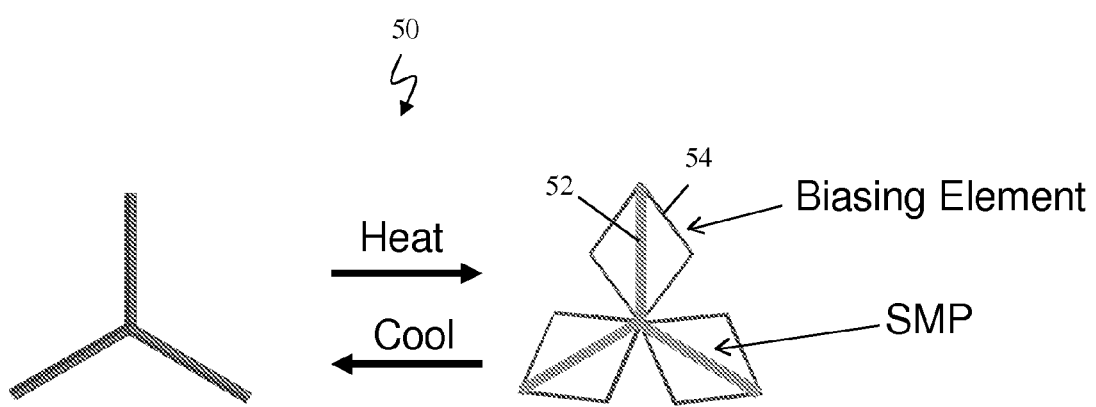
FIG. 8 is a schematic of a triple-bow actuator according to the present invention.
Figure 9:
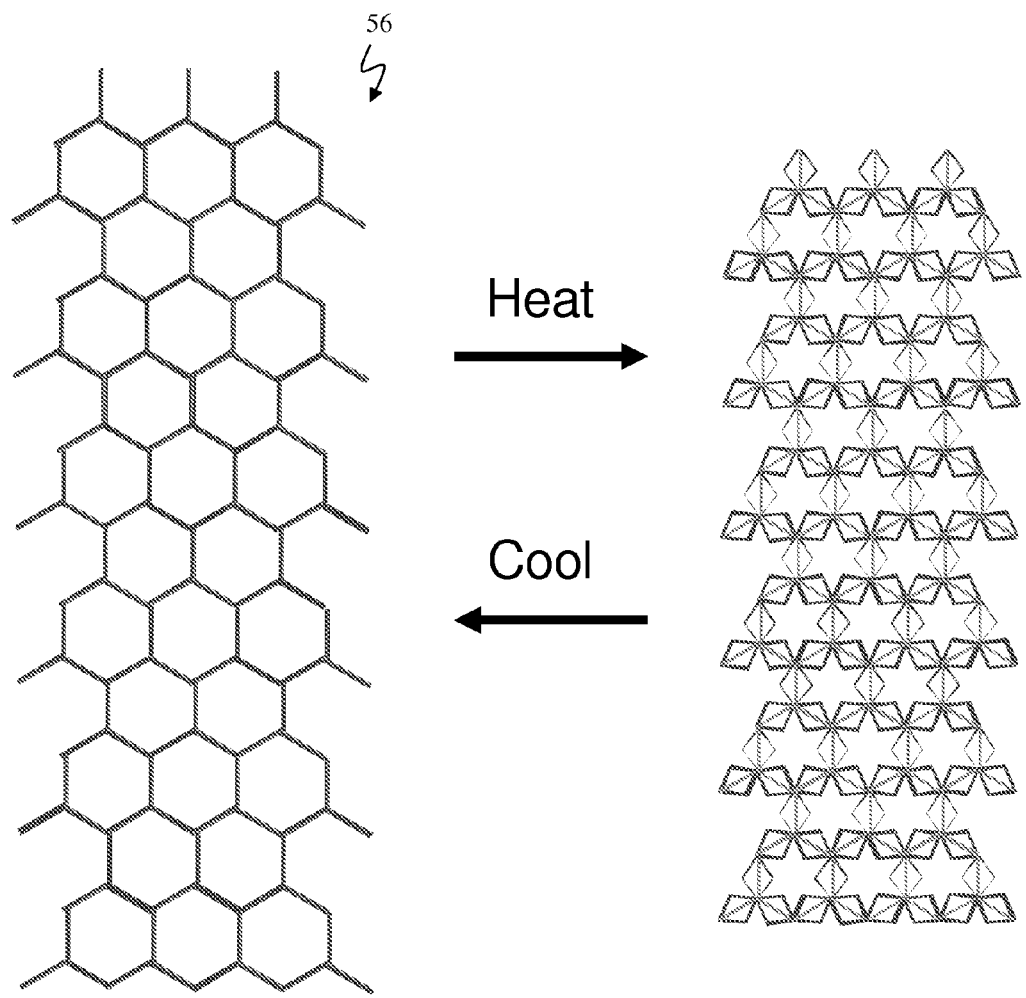
FIG. 9 is a schematic of a linear sheet of interconnected triple-bow actuators according to the present invention.

As seen in FIG. 8, two-dimensional actuators 50 that expand along a plane may be configured by forming three rods 52 from a shape memory polymer and training the rods 52 to have a contracted configuration above the shape memory transition temperature. Rods 52 are then arranged to be commonly attached at one end and extend radially outward at equal angles. Elastomeric biasing elements 54 are positioned along each shape memory rod 52 and configured to bias each rod 52 into an elongated position so that each rod 52 extends radially. Upon the application of heat above the shape memory transition temperature, rods 52 will contract against the force of the biasing elements 54. Referring to FIG. 9, actuators 50 may be interconnected in a geometric pattern to form a sheet 56 that will expand and contract along the plane of the actuators 52.

Figure 10:
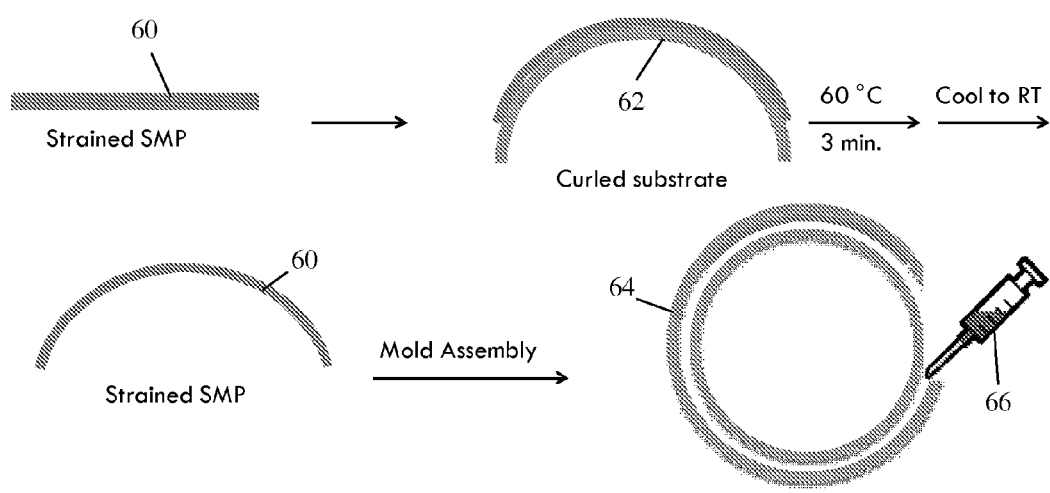
FIG. 10 is a schematic of a method for producing a linear actuator having curvature actuation alternation.

Referring to FIG. 10, bimorph curling actuators, such as those in FIG. 4B, may be formed by positioning a strained length of a shape memory polymer 60 having a flat configuration around the outside of a curved substrate 62. Shape memory polymer 60 may then be heated for a predetermined time period, such as at 60 degrees C. for three minutes, to fix its transition configuration and then cooled to room temperature. Strained shape memory polymer 60 having a curved configuration may then be placed inside the outermost inner surface of an annular glass mold 64. An elastomeric component 66 may then be injected to the annular space of mold 64 and bound to shape memory polymer 60.

Figure 11:
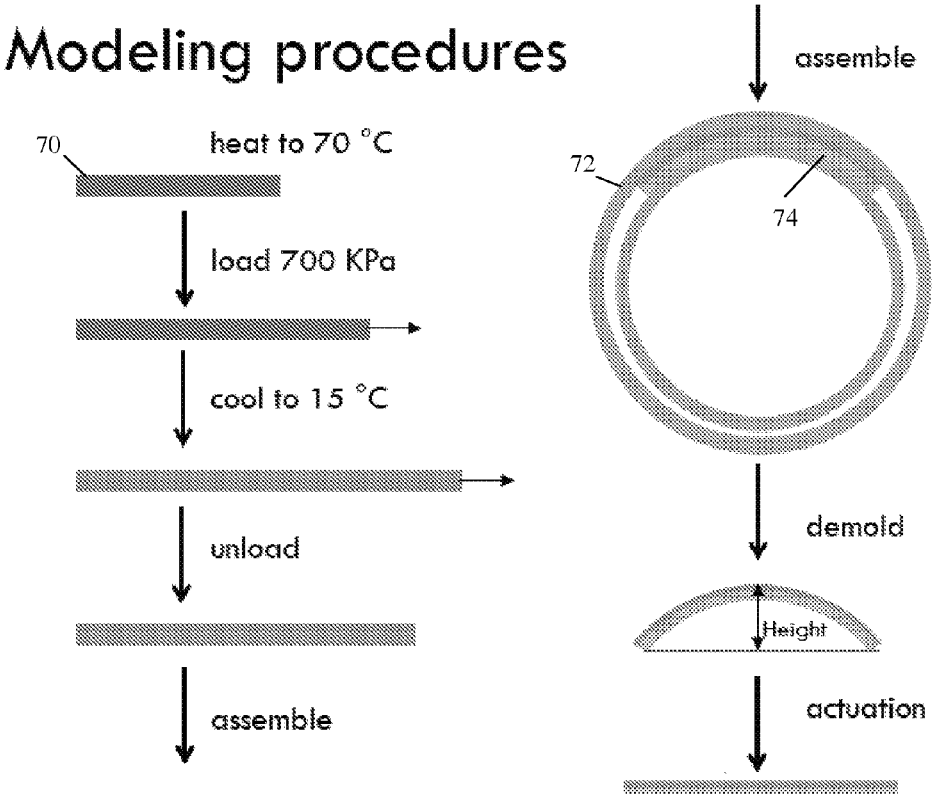
FIG. 11 is another schematic of a method for producing a linear actuator having curvature actuation alternation.

As seen in FIG. 11, another process for forming actuators according to the present invention involves heating a shape memory polymer 70 to 70 degrees C. and loading to 700 KPa to establish its permanent fixed shape. Next, shape memory polymer 70 is cooled to 15 degrees C. and unloaded. A bimorph actuator is then assembled by placing shape memory polymer 70 inside an annular glass mold 72 and bound to an elastomer 74. The resulting bimorph actuator is then demolded and will have a curled shape at the cooled temperature. Actuation with heat will induce a flattening as shape memory polymer 70 shortens and flattens elastomer 74 into a linear configuration as polymer 70 returns to the permanent fixed length.

Figure 12:
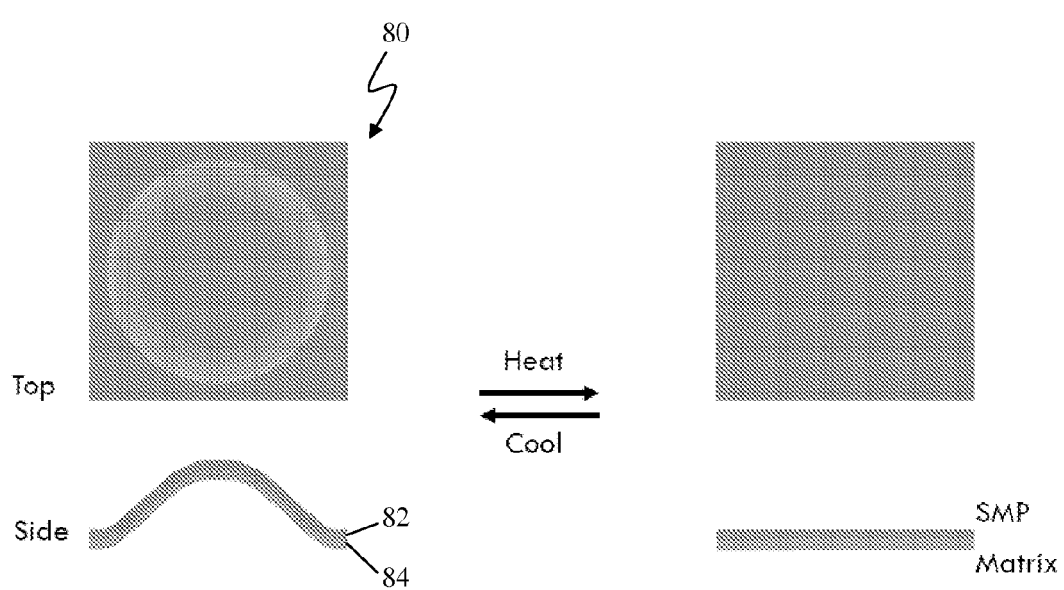
FIG. 12 is a schematic of a hemispherical actuator according to the present invention.
Figure 13:
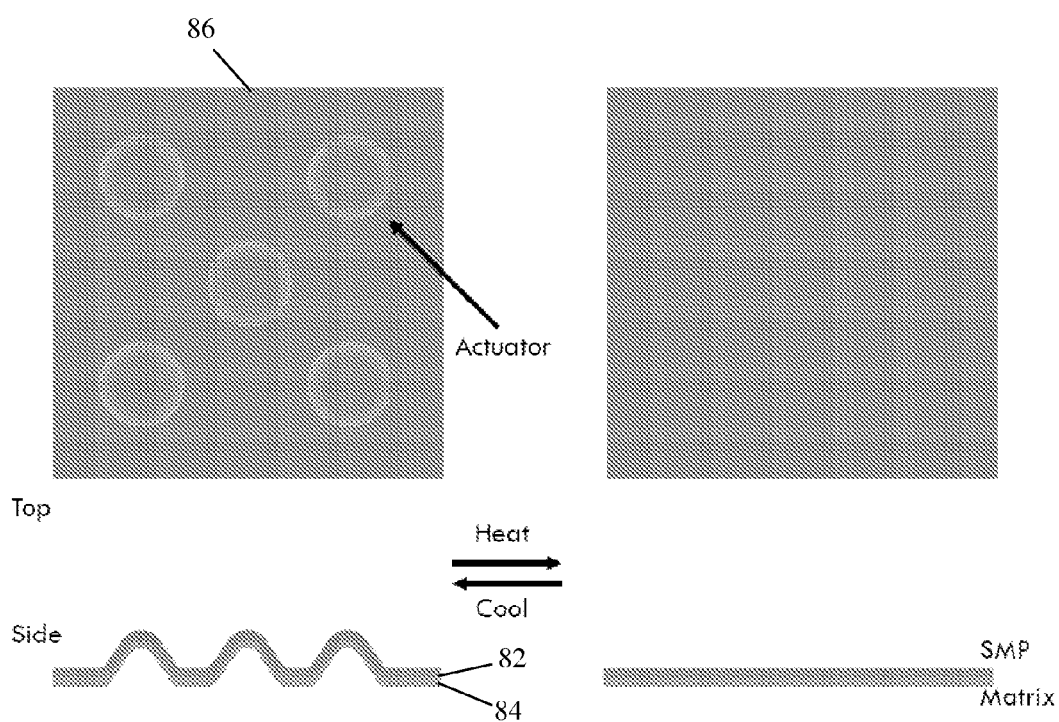
FIG. 13 is a schematic of a linear sheet of hemispherical actuators according to the present invention.

Referring to FIG. 12, the bimorph approach of the present invention can be configured as a hemispherical actuator 80 where a layer 82 of a shape memory polymer bound to a layer of an elastomer 84 is prepared to transition between a hemispherical configuration and a planar configuration in response to the application of heat above the shape memory transition temperature. As seen in FIG. 13, a plurality of hemispherical actuators 80 may be formed in a common sheet 86.

Figure 14:
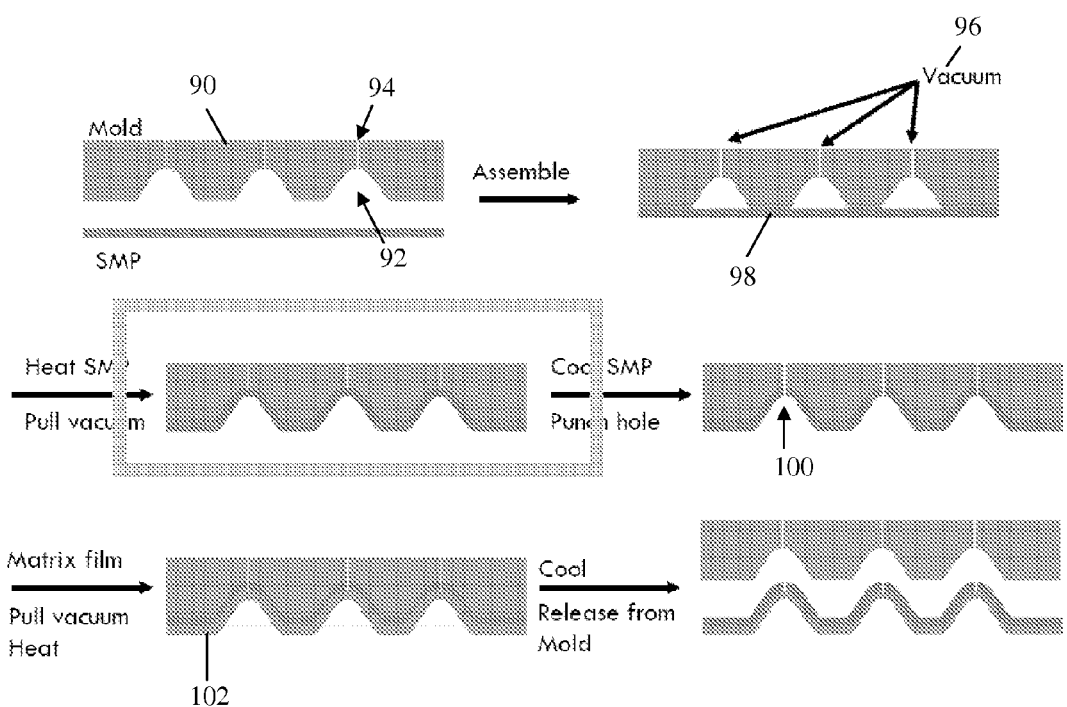
FIG. 14 is a schematic of a process for making a plurality of hemispherical actuators.
Figure 15:
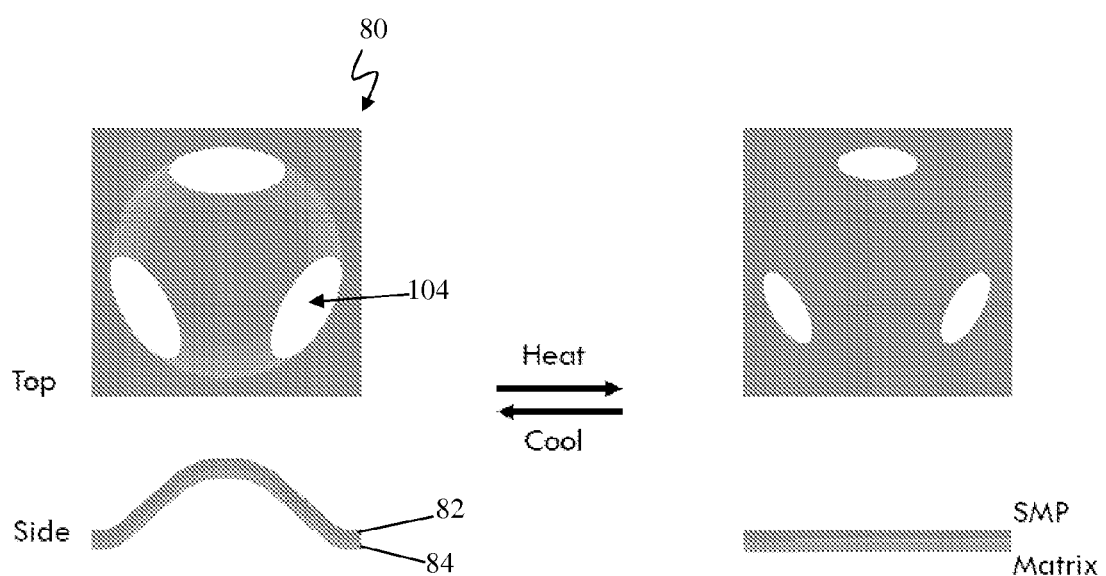
FIG. 15 is a schematic of another embodiment of a hemispherical actuator according to the present invention.

Sheet 86 of hemispherical actuators 80 may be formed using a mold 90 having a plurality of hemispherical cavities 92, each of which includes an aperture 94 formed at the zenith of hemispherical cavity 92, as seen in FIG. 14. Apertures 94 are positioned in communication with a vacuum source 96 so that a layer 98 of a shape memory polymer having a fixed planar configuration may be positioned over mold 90, heated, and then drawn into hemispherical cavities 92. Holes 100 are then punched in layer 98 at the zenith of hemispheric cavities 92 so that a vacuum can be used to draw a layer 102 of an elastomer into cavities 92 under the application of heat. The resulting bimorph sheet can be cooled and released from mold 90 to provide a plurality of hemispherical actuators 80 formed into a common sheet 86. Referring to FIG. 15, hemispherical actuators 80 may include one or more openings 104 formed therethrough to assist with the transition from the hemispherical configuration to the planar configuration by providing areas into which excess material can expand.

Figure 16:
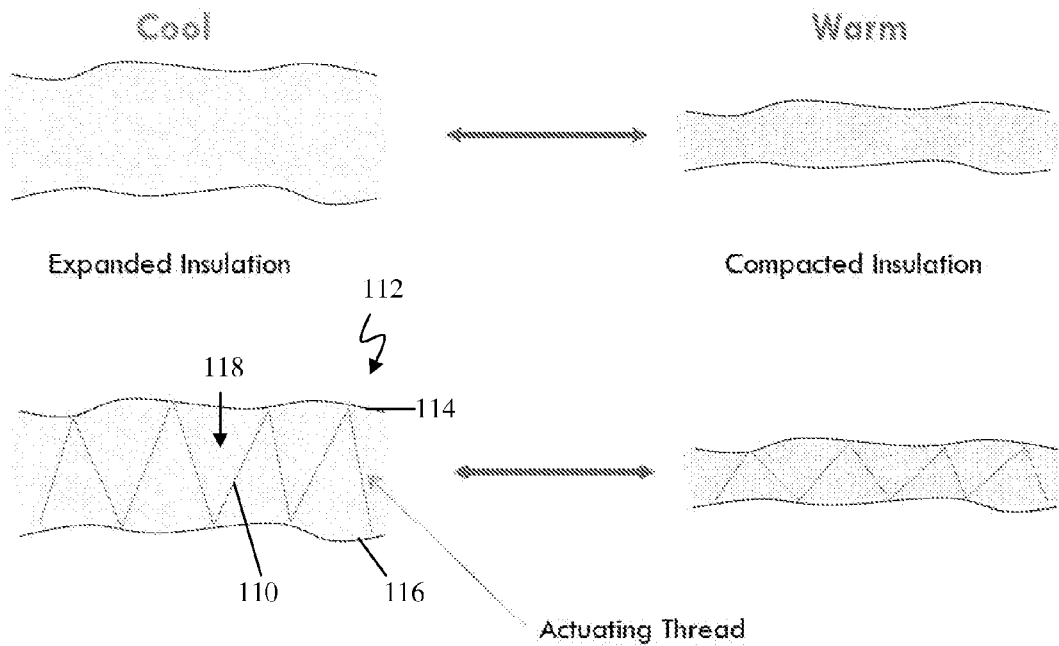
FIG. 16 is a schematic of a shape memory thread actuator system.
Figure 17:
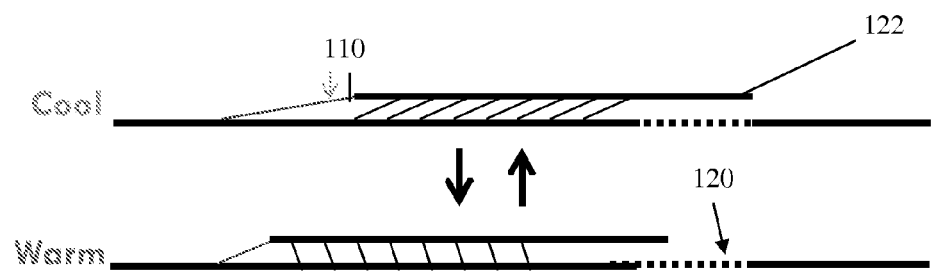
FIG. 17 is a schematic of another embodiment of a shape memory thread actuator system.

Referring to FIG. 16, the present invention also includes a shape memory thread 110 having a contracting shape memory component and a lengthening elastomeric component that may be used to induce a change in an insulated fabric 112. For example, shape memory threads 110 may be used to interconnect the inner and outer layers 114 and 116, respectively, of fabric 112 that surround the insulation 118. Threads 112 are configured to have a contracted configuration above the shape memory transition temperature and be biased into the elongated state below the transition temperature. As a result, when the fabric 112 is warmed above the transition temperature, threads 112 will contract and draw inner and outer layers 114 and 116 together, thereby compressing the insulation 118 and reducing its insulating capacity. Alternatively, as seen in FIG. 17, shape memory threads 110 may be used to selectively open and close an aperture 120 formed through a fabric 122, thereby allowing a garment made of fabric 122 to vent in response to temperatures above the shape memory transition temperature of the shape memory component of threads 110. Shape memory fibers 110 may comprise poly(cyclooctene) melt-spun fibers that are cross-linked. Crosslinked melt-spun fibers exhibit shape memory with an average of eighty-eight percent recovery of original length. Shape recovery may be improved with increased crosslinking using an electron beam process.

Figure 18:
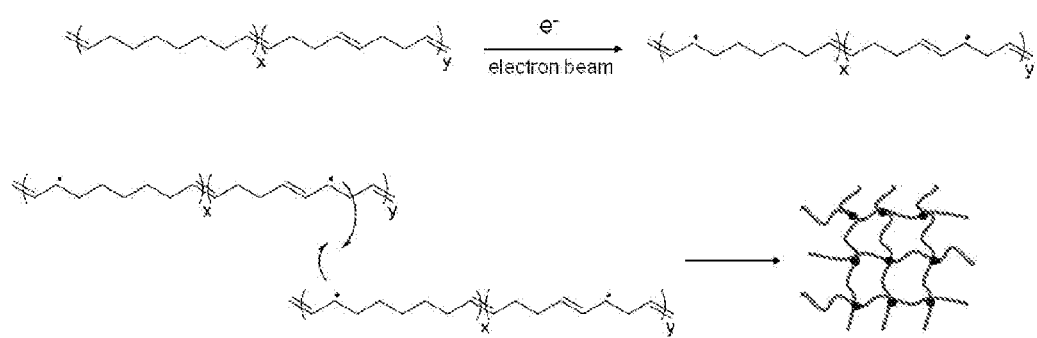
FIG. 18 is a schematic of a process for making an actuator using electron beam cross-linking according to the present invention.

Referring to FIG. 18, the present invention also involves a process for forming cross-linked shape memory polymers that eliminates the need for incorporation of a peroxide curing agent using a mixing step and provides for faster cross-linking of films by using an electron beam to induce cross-linking.

Figure 19:
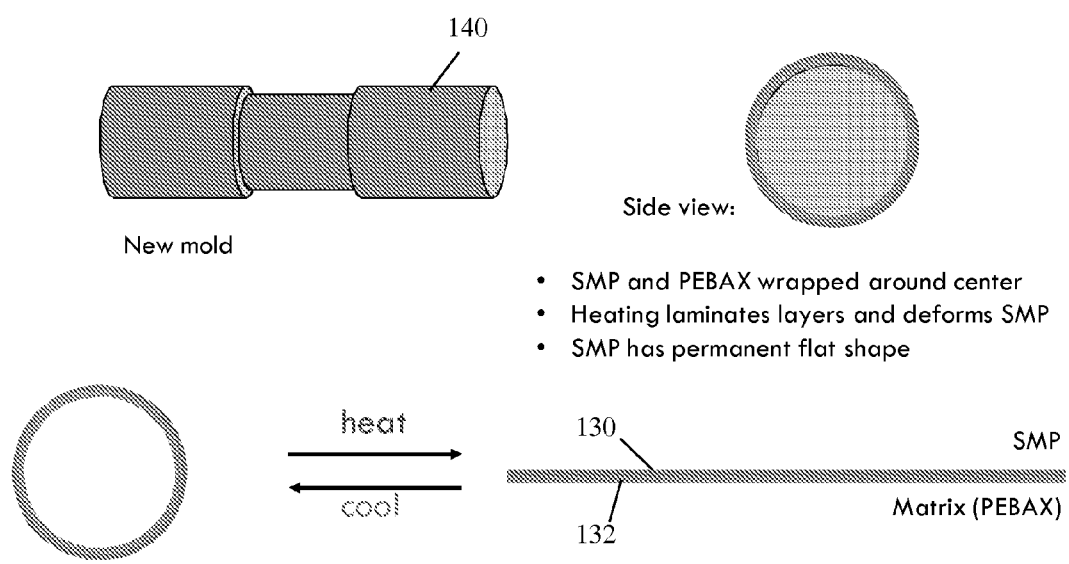
FIG. 19 is a schematic of a molding process for making a linear shape memory actuator according to the present invention.

As seen in FIG. 19, bimorph actuators according to the present invention may be molded by wrapping a first layer 130 of a shape memory polymer having a permanent flat shape and a second layer 132 of a thermoplastic elastomer, such as PEBAX® polyether block amide, around the center of a barbell shaped mold 140. Heating of mold 140 laminates layers 130 and 132 and sets the biasing of the elastomer layer 132 into a curved configuration. The resulting bimorph actuator will be curved when cool and will flatten into a planar configuration in response to heat as first layer transitions to the permanent flat shape as the shape memory transition temperature is reached or exceeded.

Figure 20:
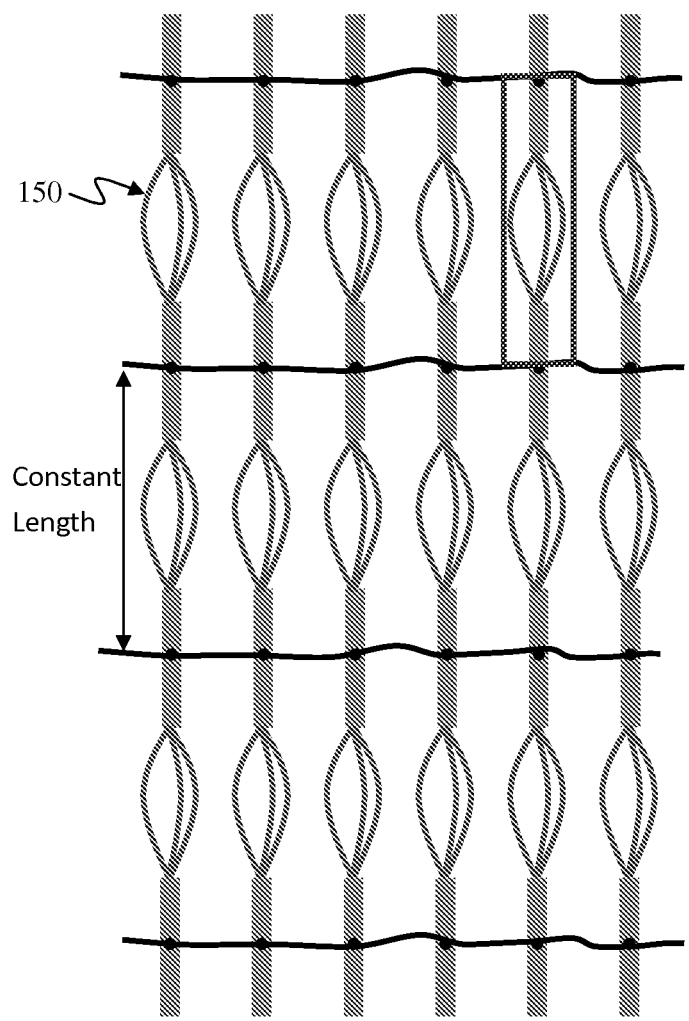
FIG. 20 is a first schematic of network of puffing actuators according to the present invention.
Figure 21:
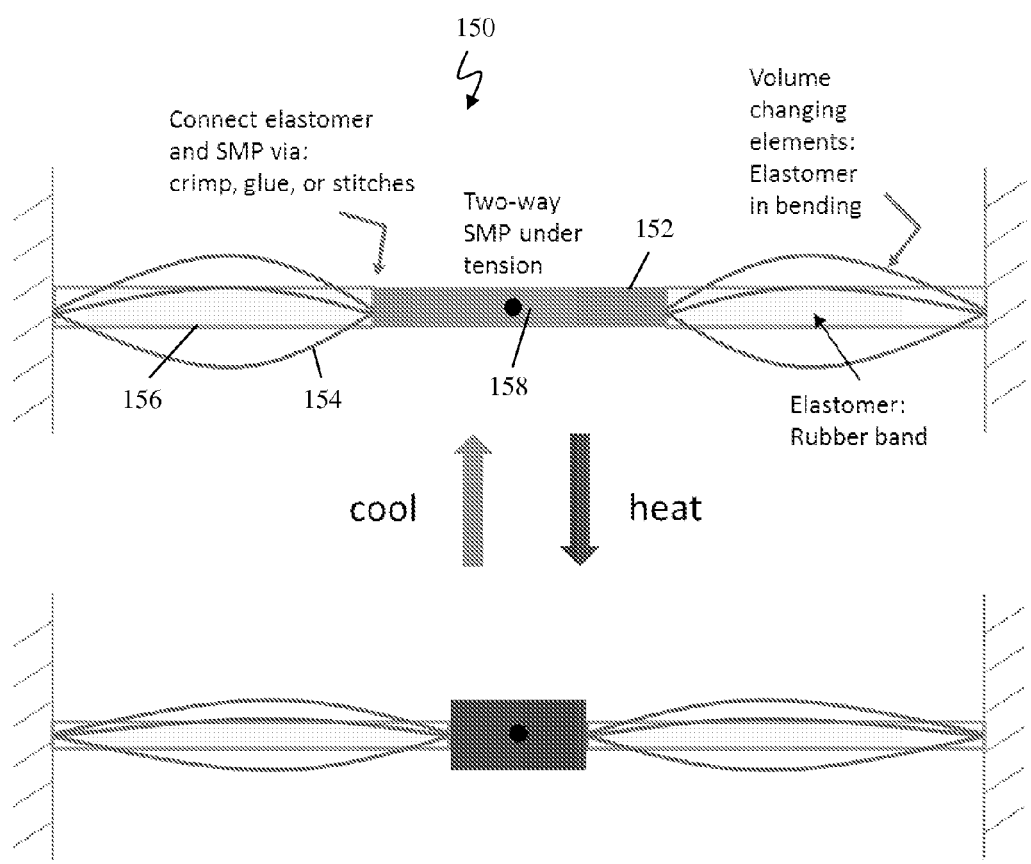
FIG. 21 is a second schematic of a network of puffing actuators according to the present invention.

Referring to FIGS. 20 and 21, the present invention includes a network of "puffing" actuators 150 comprised of a central shape memory polymer driver 152 that extends when heated and is positioned between two elastomeric volume changing portions 154, such as an axially slotted rubber tube formed from an elastomer, each of which surround a biasing elastomer 156 that cooperates with driver 152 to bias driver 152 back to its initial configuration after cooling. In response to a change in temperature, driver 152 can shorten and lengthen, thereby driving portions 154 between expanded and contacted volume configurations. Each actuator 150 may be positioned adjacent to another actuator 150 and formed into a fabric via a stitch 158 positioned at the junction between actuators 150.

Figure 22:
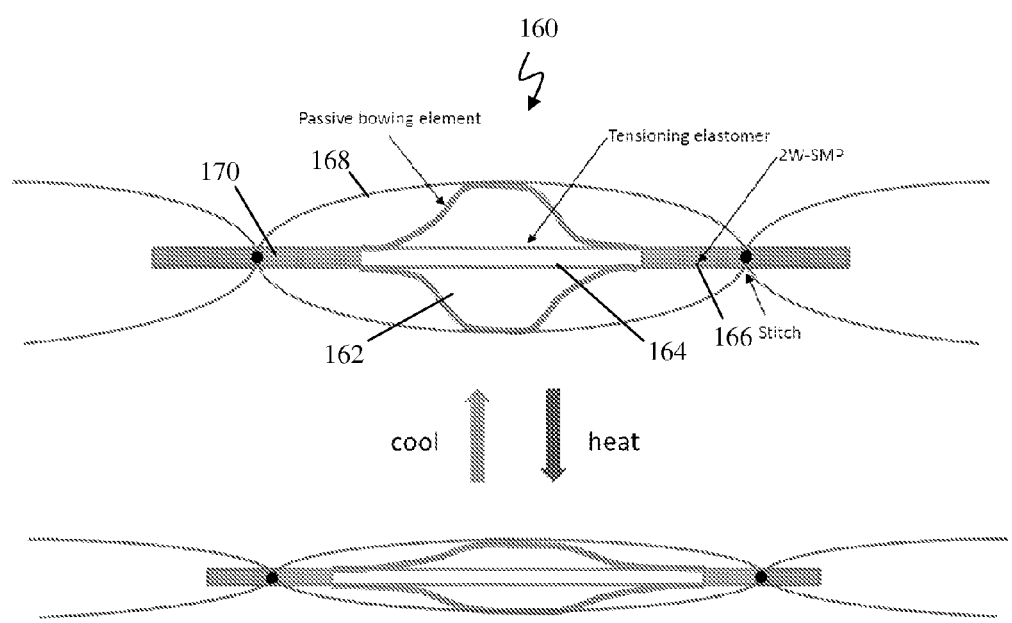
FIG. 22 is a schematic of a volumetric actuator according to the present invention.

As seen in FIG. 22, the present invention may be configured as a volumetric actuator 160 formed from a passive bowing element 162 and a tensioning elastomer 164 positioned between the ends of two opposing shape memory polymer portions 166 configured to contract when heated to the shape memory transition temperature. Bowing elements 162, tensioning elastomer 164, and opposing shape memory polymer portions 166 are enclosed within a cell 168. When heated, opposing shape memory polymer portions 166 contract, thereby reducing the volume of cell 168. When cooled, tensioning elastomer 164 returns shape memory polymer portions 166 to the elongated state, thereby allowing passive bowing elements to expand 162 and driving cell 168 into a larger volumetric configuration. As with puffing actuators 150, adjacent volumetric actuators 160 are separated by a stitch 170.

Figure 23:
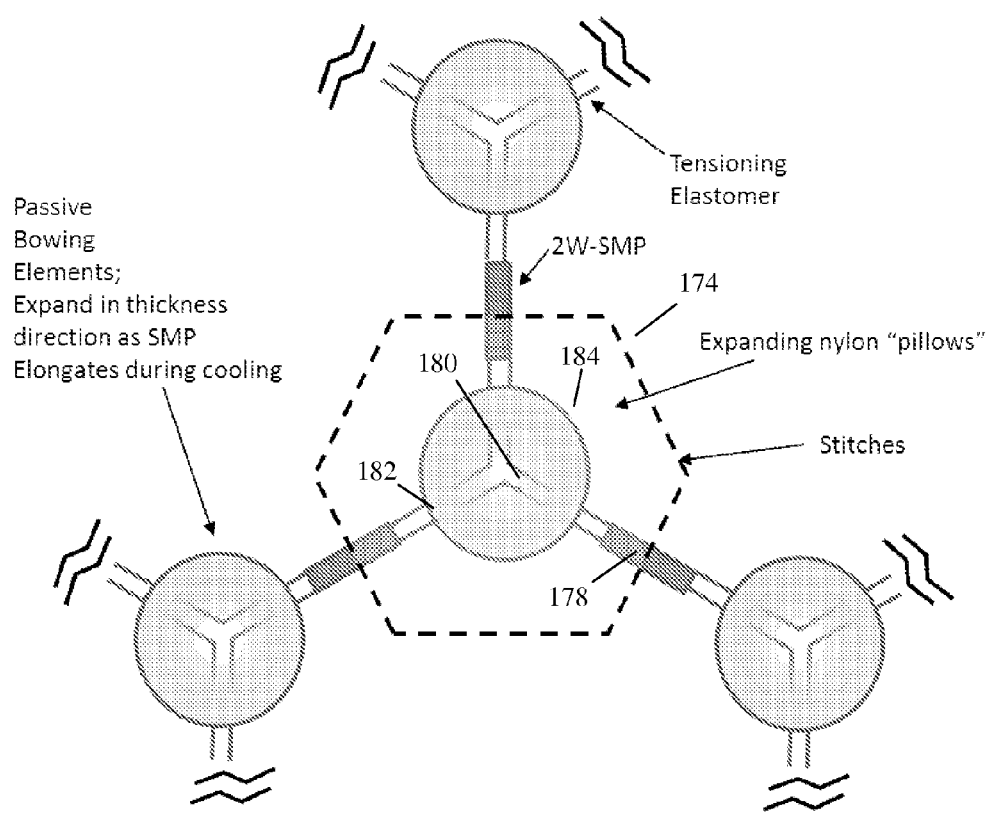
FIG. 23 is a second schematic of a volumetric actuator according to the present invention
Figure 24:
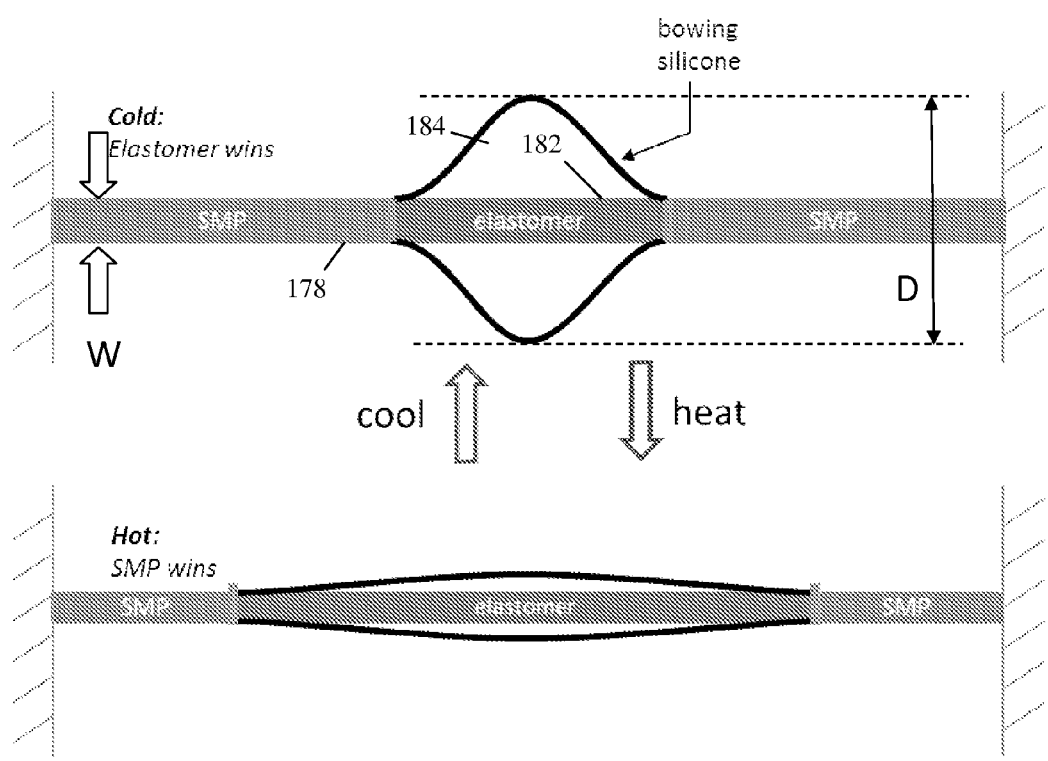
FIG. 24 is a schematic of the two dimensional actuators of a volumetric actuator according to the present invention.

Referring to FIG. 23, volumetric actuator 160 of FIG. 22 may be configured into a hexagonal pattern by defining a stitched region 174 in a layered fabric that encloses the ends of three shape memory polymer portions 178 that are interconnected to a single common point 180 by three corresponding tensioning elastomers 182 and positioned within the layers of the fabric. Bowing elements 184 expand or contract to increase or decrease the volume of air between the layers of the fabric, thereby adjusting the insulating value of the fabric. The two dimensional actions of shape memory polymer portions 178, tensioning elastomers 182, and bowing elements 184 are seen in FIG. 24. The total tension is lowered by decreasing the width, W, of both SMP and tensioning elastomer (noting that they need not be identical) but actuation amount is independent of W. The, volumetric actuators 160 should be designed to lower W as much as possible while maximizing D with enough stiffness to push any enclosing fabric.

Figure 25:
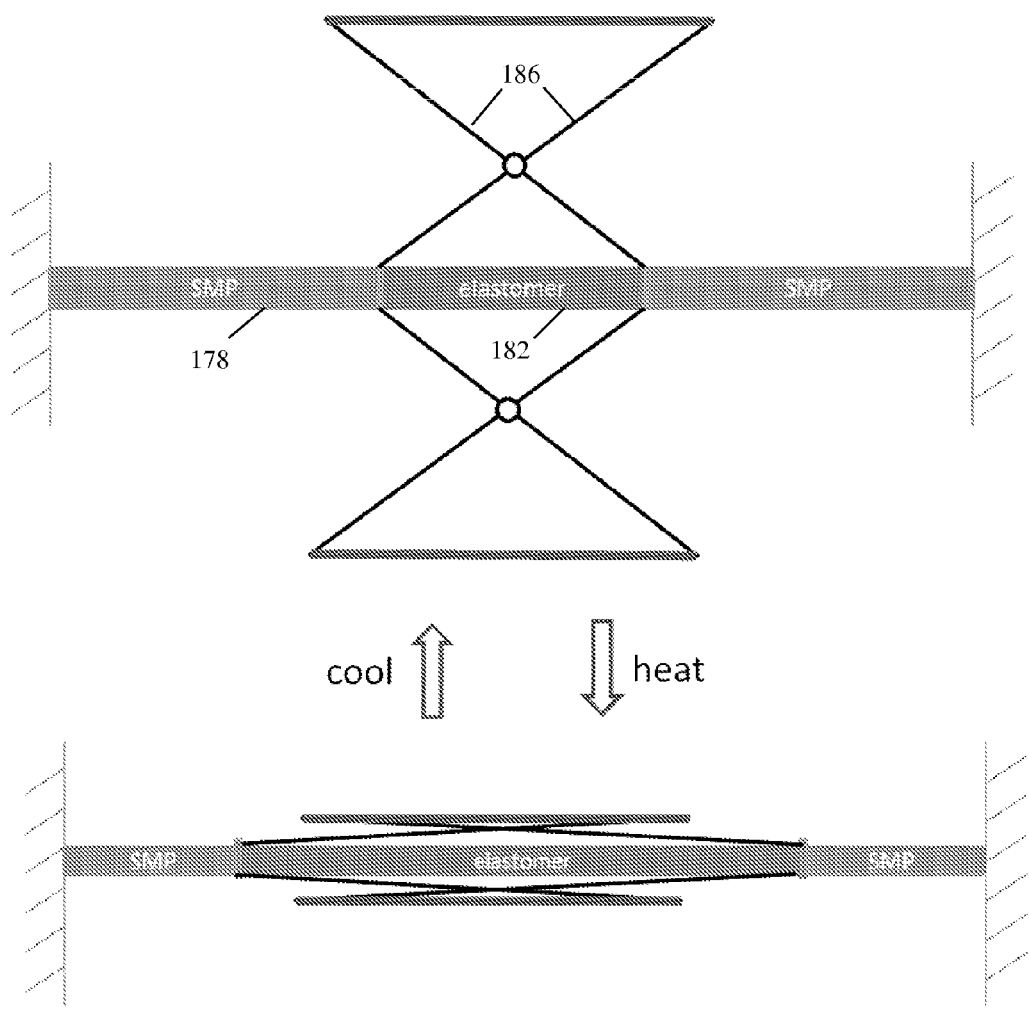
FIG. 25 is a schematic of a scissoring arm actuator according to the present invention.
Figure 26:
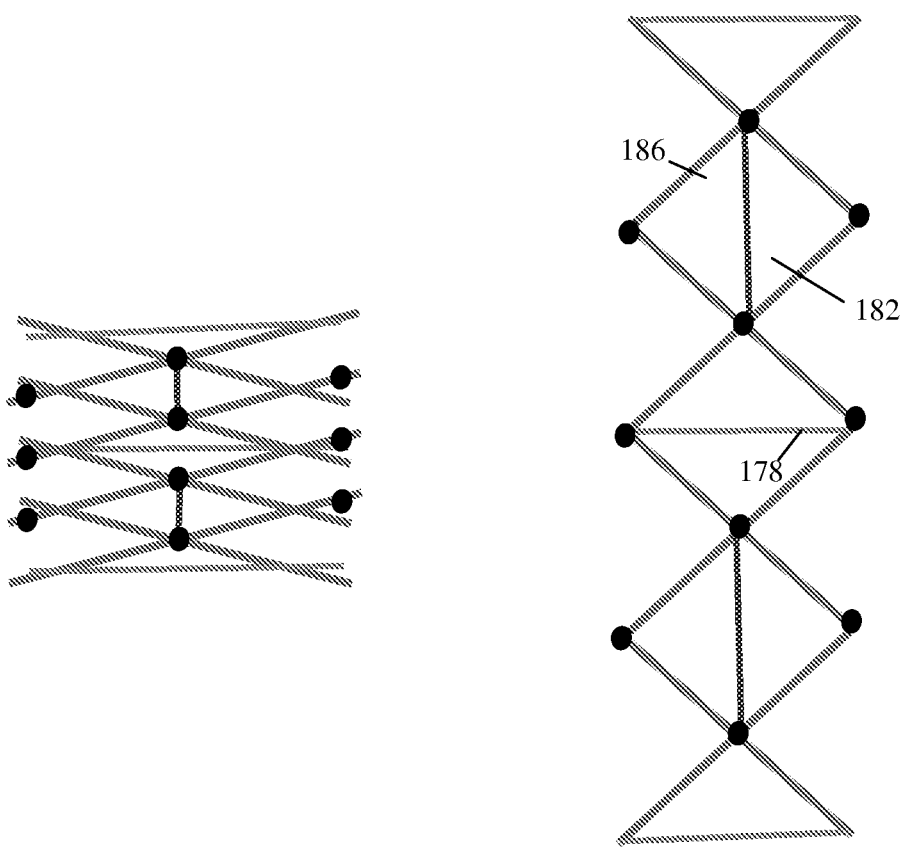
FIG. 26 is a second schematic of a scissoring arm actuator according to the present invention.

Referring to FIG. 25, bowing elements 184 may be replaced with scissoring arms 186 to increase the amount of transverse expansion and contraction created by the longitudinal movement of shape memory polymer portion 178 and tensioning elastomer 182. As seen in FIG. 26, scissoring arms 186 can instead be interconnected to shape memory polymer portion 178 and tensioning elastomer 182 in various other locations to drive the movement of scissor arms 186 between expanded and contracted configurations.

Figure 27:
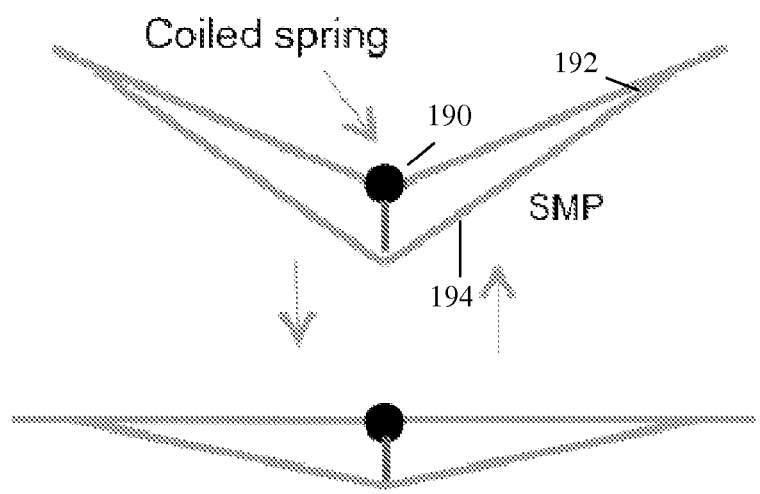
FIG. 27 is a schematic of a coil spring actuator according to the present invention.

Referring to FIG. 27, the elastomeric aspects of the present invention may be accomplished by use of a coil spring 190 having a pair of opposing arms 192 that are stiff and interconnected to the opposing end of a V-shaped shape memory polymer actuator 194. This embodiment can provide a nearly flat elevation in the heated state, does not require any lamination or bonding, and produces a large thickness change. The pair of opposing arms may be flat or curved plates configured like butterfly wings.

Figure 28:
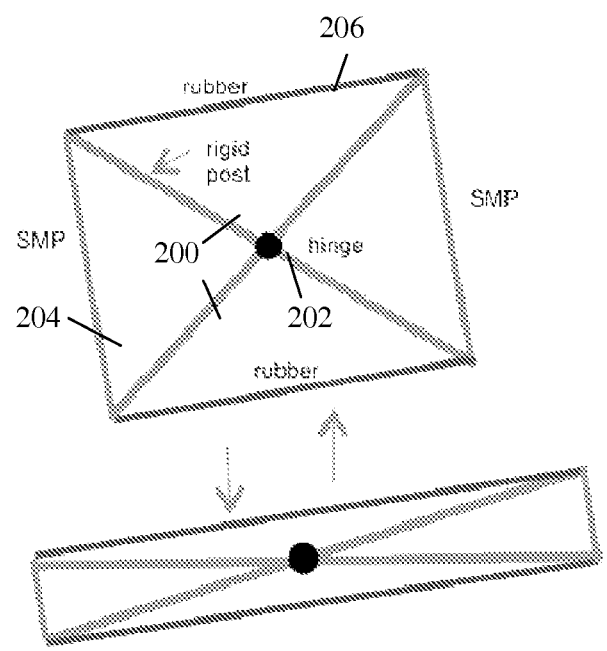
FIG. 28 is a schematic of an actuator with a pair of scissoring posts according to the present invention.

Alternatively, as seen in FIG. 28, the present invention may be configured as a pair of scissoring posts 200 or plates that pivot about a common hinge 202 and are interconnected along one set of opposing ends by a shape memory polymer element 204 and interconnected along another set of opposing ends by an elastomeric element 206, thereby allowing scissoring posts 200 to pivot between a contracted and expanded configuration. This embodiment can provide large shape changes and does not require any lamination or bonding, but will not be as flat in the heated state as other embodiments.

Figure 29:
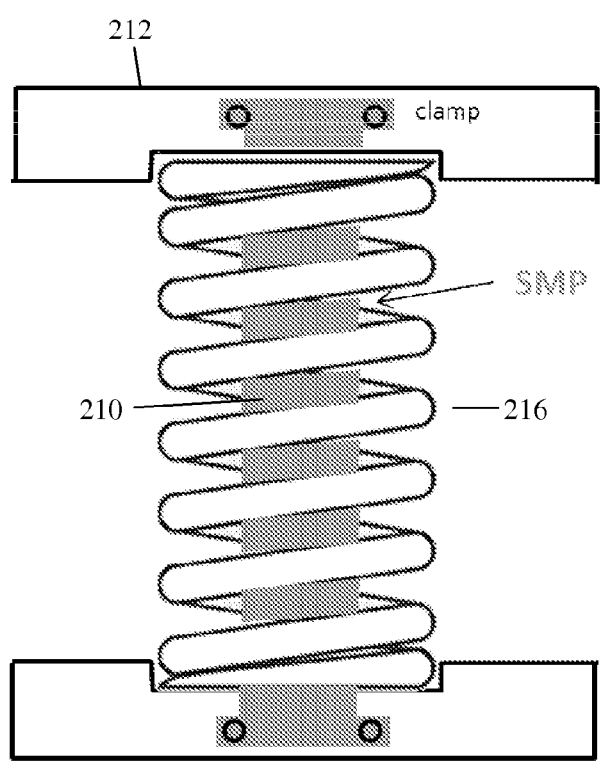
FIG. 29 is a schematic of a post actuator according to the present invention.

Referring to FIG. 29, the present invention may be configured as shape memory polymer post 210 that extends between and is interconnected to two opposing supports 212 via a clamp 214. Post 210 is configured in a stretched/fixed state and will thus contract in response to a stimulus such as heat. A coil spring 216 is positioned around post 210 and is configured to bias supports 212 outwardly against the actuating force of post 210, thereby returning supports 212 to the original position after post 210 is cooled. As with prior arrangements, the biasing forces provided by post 210 and coil spring 216 may be reversed to that supports 212 are expanded when posts 210 are heated and contracted when posts 210 are cooled.

What is claimed is:

1. A shape memory actuator, comprising:
   a first portion comprised of a shape memory polymer having a prescribed configuration above a transition temperature;
   a second portion interconnected to said first portion and comprised of an elastomer configured to bias said first layer into a temporary configuration that is different than said prescribed configuration;
   wherein said first portion transitions to said prescribed configuration over said bias of said second portion when heated above said transition temperature and said second portion biases said first portion into said temporary configuration when cooled below said transition temperature.

2. The actuator of claim 1, wherein said fixed configuration is curved and said temporary configuration is flat.

3. The actuator of claim 1, wherein said temporary configuration is curved and said fixed configuration is flat.

4. The actuator of claim 1, wherein said fixed configuration is hemispherical and said temporary configuration is planar.

5. The actuator of claim 4, wherein said hemispherical configuration includes at least one hole formed through said first and second portions.

6. The actuator of claim 1, wherein said fixed configuration is spherical and said said temporary configuration is planar.

7. The actuator of claim 1, wherein said transition temperature is between −10 degrees Celsius and 50 degrees Celsius.

8. The actuator of claim 7, wherein said transition temperature is between 10 degrees Celsius and 30 degrees Celsius.

9. The actuator of claim 1, wherein the elastic bias of said first portion and said second portion is about the same.

10. The actuator of claim 1, wherein said first portion is interconnected at one end to said second portion.

11. The actuator of claim 1, further comprising an expanding element interconnected to said second portion and configured to elongate and contract as said second portion is biased by said first portion.

12. The actuator of claim 11, wherein said elongating element comprising a flexible member that bows.

13. The actuator of claim 12, wherein said elongating member comprises a pair of scissor arms.

14. The actuator of claim 11, wherein said elongating element comprises a coil spring.

15. The actuator of claim 11, wherein said elongating element comprises a pair of pivoting rods.

16. The actuator of claim 1, wherein said elastomer is selected from the group consisting of acrylates, laminated matrix materials, neopentyl glycol propoxylate diacrylate, trimethylolpropane ethoxylate triacrylate, crosslinked poly (dimethyl siloxane), styrene-butadiene rubber, acrylic elastomers, epoxy elastomers, hydrogels, crosslinked polybutadiene, crosslinked polyisoprene, crosslinked natural rubber, and crosslinked polyisobutylene.

17. A method of forming a shape memory actuator, comprising the steps of:
   fixing a shape memory polymer to have a predetermined tensile strain;
   applying an uncured liquid elastomer to said shape memory polymer; and
   curing said uncured liquid elastomer to form elastomeric layer bound to said shape memory polymer.

18. The method of claim 12, wherein said predetermined tensile strain comprises an elongated configuration.

19. A method of forming a shape memory actuator, comprising the steps of
   positioning a layer of a shape memory polymer over a mold defining at least one cavity having a hole formed therein that is in communication with a vacuum source;
   heating said layer of said shape memory polymer;
   applying a vacuum to said mold until at least a portion of said layer of shape memory polymer is drawn into said cavity;
   punching an opening through said layer of shape memory polymer that is in communication with said hole formed in said cavity of said mold;
   positioning a layer of an elastomer over said layer of said shape memory polymer;
   heating said layer of said elastomer; and
   applying a vacuum to said mold until at least a portion of said layer of said elastomer is drawn into said mold and into contact with said shape memory polymer layer.

20. The method of claim 13, wherein said cavities in said mold are hemispherical in shape.

* * * * *